United States Patent [19]

Buddemeyer

[11] 4,246,352
[45] Jan. 20, 1981

[54] TEST SAMPLE CONTAINER

[76] Inventor: Edward U. Buddemeyer, 11507 Notch Cliff Rd., Glenarm, Md. 21057

[21] Appl. No.: 970,801

[22] Filed: Dec. 18, 1978

[51] Int. Cl.² .............................................. C12M 1/34
[52] U.S. Cl. .................................... 435/291; 435/35; 435/296; 435/299; 435/808
[58] Field of Search ...................... 195/127, 139, 103.7, 195/103.5; 424/1.5; 435/291.35, 807, 808, 253–255, 299, 300, 296

[56] References Cited

U.S. PATENT DOCUMENTS

| | | | |
|---|---|---|---|
| 3,676,679 | 7/1972 | Waters | 195/127 |
| 3,819,489 | 6/1974 | Kronick | 195/127 |
| 3,844,894 | 10/1974 | Kronick | 195/127 |
| 3,941,660 | 3/1976 | Mirsky | 195/127 X |
| 3,944,471 | 3/1976 | Waters | 195/127 X |
| 3,997,404 | 12/1976 | Waters | 195/127 X |
| 4,057,470 | 11/1977 | Schrot | 195/127 |

OTHER PUBLICATIONS

Buddemeyer, "Liquid Scintillation Vial for Cumulative & Continuous Radiometric Measurements of in Vitro Metabolism", Applied Microbiology, Aug. 1974, pp. 177–180.

*Primary Examiner*—R. B. Penland
*Attorney, Agent, or Firm*—Lane, Aitken, Ziems, Kice & Kananen

[57] ABSTRACT

The present invention provides a test sample container for measuring the biological activity of cells, bacteria, or micro-organisms in a test sample by radiometric techniques. The container is suited for use with automated laboratory equipment and provides greatly improved measurement efficiency over prior designs. In one embodiment, the test sample container includes a serum vial adapted to contain a quantity of a test sample and a radionuclide-labeled nutrient media. A micro-tube, which contains a mixture of a gas absorber and a scintillation compound, is positioned above the surface of the sample/media mix by a split-skirt stopper that also serves to seal the serum vial. The gas metabolized or otherwise evolved by the micro-organisms in the test sample is absorbed by the absorber in the micro-tube causing the scintillation compound to emit light flashes at a rate proportional to the quantity of radioactive gas absorbed. These light emissions are detected and counted in a conventional scintillation counter and provide a continuous indication of the radiorespirometric profile of the micro-organisms.

12 Claims, 6 Drawing Figures

ABSORBER/
SCINTILLATION
COMPOUND

SAMPLE/NUTRIENT
MEDIA

ABSORBER/
SCINTILLATION
COMPOUND

TEST SAMPLE CONTAINER

BACKGROUND OF THE INVENTION

1. Field of the Invention

The present invention relates to an apparatus for detecting and measuring the biological activity of microorganisms in a test sample by radiometric techniques and, more specifically, to a test sample container which includes an absorber/scintillation compound positioned relative to the test sample to provide improved measuring efficiency.

2. Prior Art

Radiometric techniques have found wide-spread applications in the biological, medical, food processing and related fields as a method for detecting and measuring biological activity in a test sample. The technique generally involves innoculating a test sample containing or believed to contain bacteria or micro-organisms with a radionuclide or isotope-labeled nutrient media. The micro-organisms metabolize, oxidize, or otherwise process the nutrient media and evolve or respirate a gaseous compound which includes the radioisotope as one of its constituents. Quantitative measurement of this evolved gas and the rate at which it is evolved provides an indication of the presence of and the activity of the microorganisms in the test sample.

The labeled gas metabolically produced by the microorganisms is generally measured by scintillation techniques which involve absorbing the labeled gas in the presence of a scintillation compound or fluor. Light flashes are emitted by the scintillation compound as a function of the quantity of radio-labeled gas that is absorbed. These flashes may then be counted in a conventional laboratory scintillation counter.

A number of often complex laboratory-type devices have been developed for carrying out the above described radiometric techniques. Some of these devices are "one-shot" types in which the experiment must be terminated in order to perform the measurement and are consequently not capable of providing continuous and cumulative text tracking of a sample. Other of these devices require skilled laboratory handling procedures to ensure accurate measurements or cannot be adapted to automatic measurement using scintillation counters which have an automatic sample-vial transport mechanism.

One apparatus, developed by the present inventor, does provide continuous and cumulative tracking and is suitable for use with the automatic sample transports of conventional laboratory scintillation counters. This device is described in an article entitled "Liquid Scintillation Vial for Cumulative and Continuous Radiometric Measurement of In Vitro Metabolism" published by the present inventor in *Applied Microbiology*, August 1974, pp. 177-180. A similar device is described in U.S. Pat. No. 3,944,471 to Waters. This device includes a first container, e.g., a 30 ml. serum vial, which is adapted to contain the test sample and the nutrient media, and a second container, e.g., a standard scintillation vial, into which the first container is inserted. In one embodiment, a cylindrically formed filter paper, treated with a mixture of an absorber and a scintillation compound, is inserted into the annular space between the outside surface of the serum vial and the inside surface of the scintillation vial. The scintillation vial is then sealed with a gas impermeable closure and the device innoculated with a mixture of the test sample and radio-labeled nutrient-media by means of a hypodermic syringe inserted through the closure. Gas metabolized or fermented as a consequence of the biological activity of the micro-organisms in the test sample fills the available volume between the two containers and is absorbed onto the cylindrical filter paper. The scintillation compound emits light flashes in response to the presence of the radioactive gas absorbed on the filter paper. These flashes, when the vial is mounted in the test well of a conventional laboratory-type scintillation counter, are detected by the counter's photomultiplier tubes and counted to provide a continuous and cumulative quantitative indication of the bacterial activity.

While the above described test sample container provides an acceptable level of measurement efficiency, its structural arrangement is such that a portion of the light flashes emitted by the scintillation compound will not be detected. All conventional liquid scintillation counters use two diametrically opposed photo-multiplier tubes designed to operate in coincidence; that is, a light flash will be registered as a count if, and only if, both tubes simultaneously detect a scintillation flash. The reduction in efficiency can occur, e.g., when a light flash is emitted on one side of the filter paper support with portions of the light energy directed simultaneously towards both photo-multipler tubes. In one case, the light energy passes through the transparent wall of the scintillation vial to be detected by one of the photo-multiplier tubes, and, in the other case, the light energy passes in the opposite direction through the test sample/nutrient media mix that, in many cases, is opaque or only semi-transparent (e.g., blood), causing the light energy emitted toward the second photo-multiplier tube to be absorbed or color quenched in the test sample/nutrient media mix. Another type of quenching, known as chemical quenching, can occur when the light energy impacts long-chain organic molecules in an otherwise transparent test sample/nutrient media mix.

In addition to these count efficiency limitations, the above described design possesses a number of practical drawbacks. The filter paper cylinder and the test sample vial are not secured relative to one another or to the scintillation vial. As a result, it is possible for these two elements to shift position during a test and adversely affect the accuracy of the test and, of course, damage one or the other. The use of cylindrically-formed filter-paper support having a rather large surface area requires that the absorber/scintillation-compound mix be carefully applied over the entire surface of the cylinder to ensure uniform distribution and also requires that a larger than preferably amount of relatively expensive scintillation compound be used with each test sample container.

SUMMARY OF THE INVENTION

In view of the above, it is a broad, overall object of the present invention to provide a test sample container for effecting radiometric measurement of the biological activity of a test sample.

It is another object of the present invention to provide a test sample container for the continuous and cumulative radiorespirometric measurement of the biological activity of micro-organisms in a test sample.

It is still another object of the present invention to provide a test sample container for the radiometric measurement of biological activity of a test sample containing or believed to contain micro-organisms having an improved measurement efficiency.

It is a further object of the present invention to provide a test sample container for measuring the radiometric activity of a biological sample in which degradation of the measurement efficiency associated with color and chemical quenching is eliminated.

It is a further object of the present invention to provide a test sample container for the radiometric measurement of biological activity of a test sample which is ideally suited for automatic laboratory techniques including the automatic sample transports of laboratory scintillation counters.

It is a still further object of the present invention to provide a test sample container for the radiometric measurement of biological activity of a test sample which is inexpensive to manufacture, suitable for mass production techniques, and which has a rugged structure that can be safely transported and stored without special handling precautions.

It is still a further object of the present invention to provide a test sample container for radiometric measurement of biological activity of a test sample which may be effectively used by laboratory personnel having a minimum of laboratory skills.

In accordance with these objects, and others, the present invention provides, in one embodiment, a test sample container which includes a first container adapted to receive a selected quantity of a bacterial test sample containing or believed to contain micro-organisms and a radionuclide-labeled nutrient media that can be metabolized by the micro-organisms to produce or evolve a gas including the radionuclide. A second container, which contains a mixture of a gas absorber and a scintillation compound or fluor is located within the first container in a plane axially spaced from the test sample/nutrient medium mixture. Gas metabolized or otherwise evolved by the micro-organisms is absorbed by the absorber causing the scintillation compound to emit scintillation flashes. The position of the absorber/scintillation compound relative to the test sample/nutrient media eliminates chemical or color quenching and permits improved continuous-and-cumulative measurement efficiency in coincidence-type scintillation counters using a plurality of photo-multiplier tubes.

BRIEF DESCRIPTION OF THE DRAWINGS

The above description, as well as further objects, features, and advantages of the present invention will be more fully appreciated by reference to the following detailed description of presently preferred, but nonetheless, illustrative embodiments, in accordance with the present invention, when taken in connection with the accompanying drawings wherein.

DETAILED DESCRIPTION OF THE PREFERRED EMBODIMENTS

Figure 1:
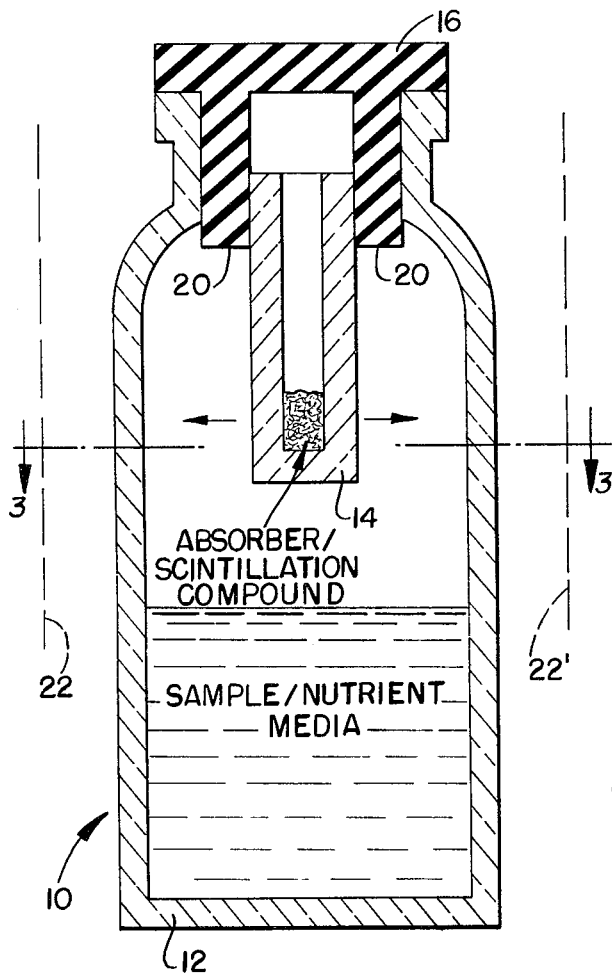
FIG. 1 is a side-elevational view, in cross-section, of a first embodiment of the present invention.
Figure 2:
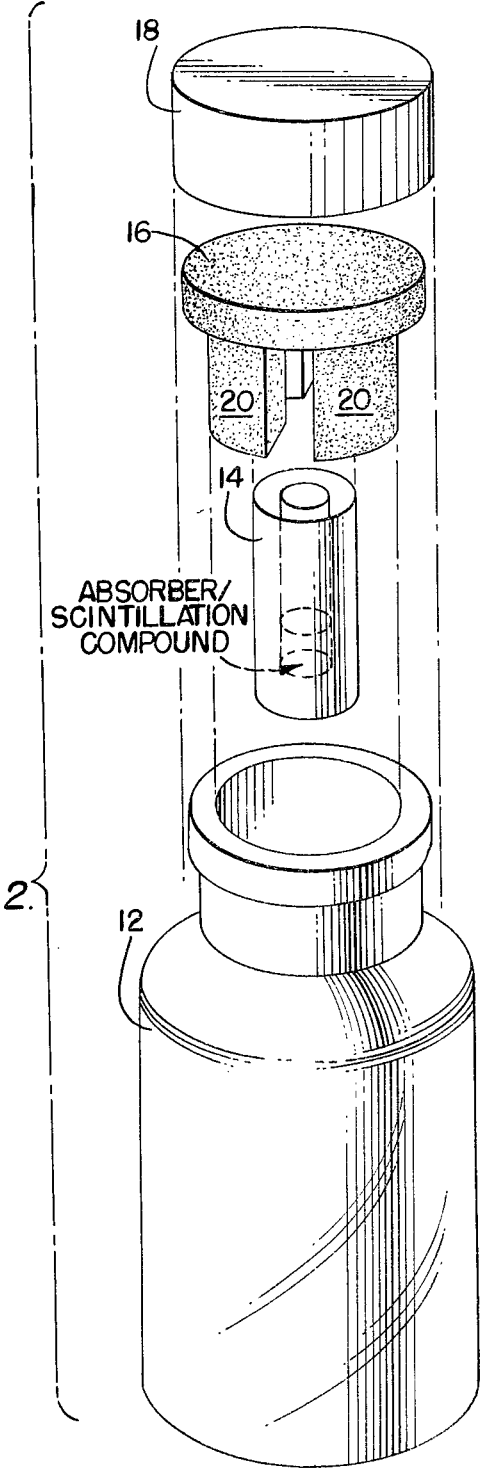
FIG. 2 is an exploded-perspective view of the embodiment illustrated in FIG. 1.

A sample test container, generally designated by the reference character 10, in accordance with the present invention is shown in FIGS. 1 and 2 and includes an outer container 12 adapted to contain a selected quantity of a bacterial test sample and a nutrient media; an inner container 14 which is adapted to contain a mixture of an absorber and a scintillation compound; and a closure member 16 which closes or plugs the outer container, supports the inner container relative to the outer container, and functions as a septum or membrane through which the test sample may be introduced into the outer container 12.

In the preferred embodiment, the outer container 12 is preferably a standard laboratory 30 ml. serum vial, the inner container 14 is preferably a 7 mm. (O.D.) micro-tube, and the closure member 16 is a standard split-skirt rubber stopper designed to plug the serum vial. A conventional aluminum crimp-cap 18 (FIG. 2) may be provided to secure the closure member 16 to the outer container 12. The inner container 14 is designed to be inserted between the depending segments 20 of the split-skirt stopper 16 and frictionally engaged therebetween such that the inner container 14 is securely located at a position above the level of the test-sample and nutrient-media mixture and approximately coaxial with the longitudinal axis of the outer container 12. The inner container 14 is open at its top and is in gas phase communication with the interior of the outer container 12 through the spaced defined between the depending segments 20 of the split-skirt stopper 16.

The outer container 12 is designed to hold a selected quantity of a test sample, e.g., blood, urine, spinal fluid, food samples, or the like, for which the biological activity is to be determined. The test sample is supplied and mixed with a nutrient media or broth that the micro-organisms in the test sample, if any, are capable of metabolizing or processing into a gas. The nutrient media is labeled with a radionuclide or radio-isotope such that the gas evolved or metabolized by the micro-organisms in the test sample will contain the radionuclide. A suitable nutrient media for a wide variety of micro-organisms preferably includes carbon atoms in which some or all of the carbon atoms have an atomic weight of 14. A nutrient media of this type can be metabolized by most micro-organisms to respirate or evolve $^{14}Co_2$ by known or unknown pathways. Examples of such nutrient media includes radio-labeled sugars, such as sucrose, fructose, xylose, maltose, lactose and the like which can be mixed with other substances including starches, nitrogen sources, and pH buffers. Other nutrient media can include amino acids, peptides, proteins, enzymes, and fatty acids. While most micro-organisms can metabolize nutrient media of the type having carbon atoms, other micro-organisms may require a nutrient media specific to their metabolic cycle and a different radionuclide including, for example, a radionuclide such as sulphur having an atomic weight of 35.

The inner container 14 is adapted to hold a selected quantity of an absorber/scintillation compound or fluor. The absorber is selected such that it absorbs the gas evolved or metabolized by the micro-organisms residing in the test sample. Absorbers suitable for the absorption of $CO_2$ generally include alkalis including calcium hydroxide, sodium hydroxide, potassium hydroxide and substances such as ethanolamine, hydroxy ethylamine and hyamine. The scintillation compound or fluor residing in the inner container with the absorber may include a wide variety of naturally occurring or commercially prepared materials adapted to emit scintillation flashes in response to the presence of the absorbed radionuclide. Suitable scintillation materials include, e.g. anthracene; 2,5-diphenyloxazole-1,4-bis-(5-phenyloxazoly)-benzene (PPO-POPOP); and various commercially-available scintillator plastics, glasses or other scintillation materials which may be formed, e.g., as beads, filaments, crystals or amorphous masses. The preferred absorber/scintillator mixture for the inner container 14 in accordance with the present invention is a mixture of sodium hydroxide and scintillation-grade anthracene, which mixture is introduced into the inner container 14 as a water slurry. The excess water is aspirated and the absorber/scintillator mixture dried in a desiccator. Anthracene is preferred because it can be heat sterilized in an autoclave in situ without an appreciable loss in efficiency. This is an important advantage since test sample containers in accordance with the present invention can be assembled on a non-sterile assembly line with their absorber/scintillator mixture and terminally sterilized in the assembled state.

The test sample container 10 of FIGS. 1 and 2 may be used to determine the bacterial activity of a test sample by innoculating a bacterial test sample into an assembled, sterile container 10 with a hypodermic syringe with the needle of the syringe passing through the closure member 16. The needle is directed into the space between the depending segments 20 of the split-skirt stopper 16 and away from the inner container 14. This permits direct deposition of the test sample onto the bottom surface of the outer container 12 and avoids disturbing or dislodging the inner container 14. The radio-labeled nutrient media may likewise be introduced into the test container by innoculation, either simultaneously with the test sample or through a separate innoculation. In the alternative, the test sample container 10 may be manufactured with a selected quantity of a standard nutrient media, in a liquid or a dehydrated form in the outer container. If the nutrient media is supplied in a dehydrated form, fluid, e.g., water, sufficient to reconstitute the nutrient media may be introduced with the innoculation of the test sample or by separate innoculation. After innoculation(s) is effected, the micro-organisms present in the test sample begin metabolizing the nutrient media and, in the case of nutrient medias which include carbon atoms having atomic weight of 14, evolve or respirate $^{14}CO_2$. This gas fills the headspace above the test sample/nutrient mixture, passes into the passages between the depending segments 20 of the closure member 16 and into the lumen of the inner container 14. The $^{14}CO_2$ is absorbed by the absorber with the carbon 14 atoms exciting the scintillation material to cause it to emit light flashes. When the test sample container 10 is inserted into the well of a conventional laboratory type scintillation counter, the light flashes can be detected by the counter's photomultiplier tubes, schematically represented by the parallel dashed lines 22—22' in FIG. 1, and quantitatively counted to provide an indication over time of the bacterial activity of the test sample. Since the test sample container 10 is closed, the light flashes emitted by the scintillation compound provide a continuous and cumulative indication of the respirometric activity of the micro-organisms in the test sample.

Figure 3:
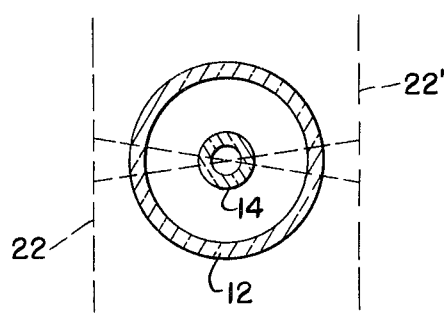
FIG. 3 is a plan view, in cross-section, of the first embodiment of the present invention taken along line 3—3 of FIG. 1.

From the performance standpoint, locating the absorber/scintillation compound mixture in a clear transparent container located in a plane that is spaced above the planes occupied by the test sample/nutrient media mixture eliminates the problems associated with color and/or chemical quenching of the light emissions to provide an enhanced counting efficiency. It is believed that the use of a transparent inner container having inner and outer diameters functions as a lenticular element to further increase the counting efficiency. For example, as shown in FIG. 3, segments of the inner container between the crossed, dotted lines define a meniscus-type lens which enhances transmission of light to the faces of the photomultiplier tubes 22–22'.

Figure 4:
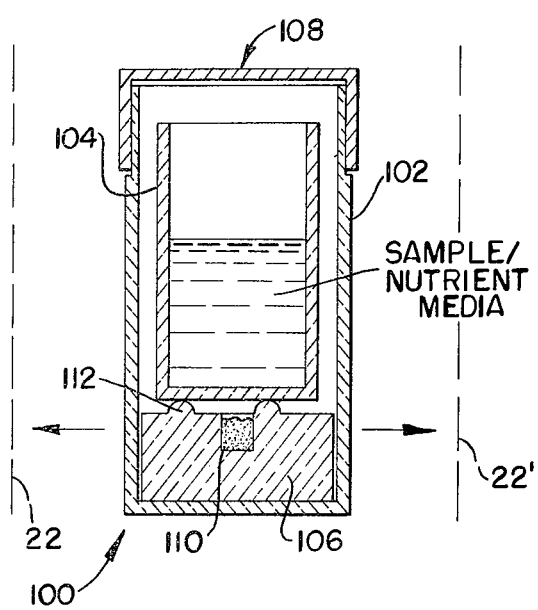
FIG. 4 is a side-elevational view, in cross-section, of a second embodiment of the present invention.
Figure 5:
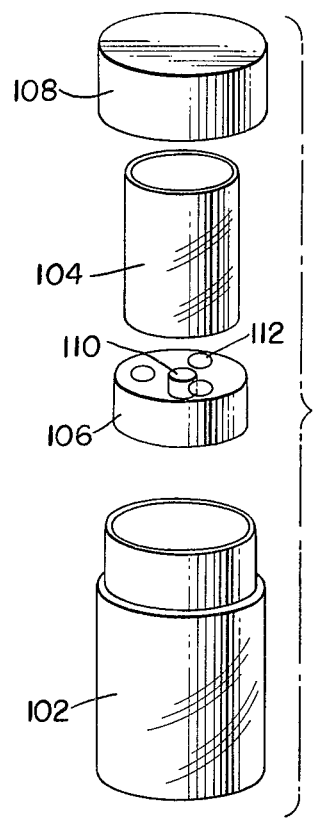
FIG. 5 is an exploded-perspective view of the embodiment illustrated in FIG. 4.

Another embodiment of the test sample container, generally designated by the reference character 100, is shown in FIGS. 4 and 5 and includes an outer container 102, an inner container 104 adapted to contain the nutrient media and test sample; a combined inner container and absorber/scintillation compound support disc 106; and a closure member 108. In the preferred form, the outer container 102 is a standard scintillation vial, and the inner container 104 is a standard serum vial adapted to fit within the outer container. The support disc 106 is preferably fabricated as a cylindrical element from a transparent molded glass or plastic material, e.g., polystyrene, and is so dimensioned as to fit within the outer container 102. The support disc 106 includes a central well 110, which contains a selected quantity of an absorber/scintillation compound, and, in the case of the preferred embodiment, three upwardly extending buttons or nubs 112 which are adapted to contact the bottom surface of the inner container 104 and support the inner container a selected distance above the upper surface of the support disc 106 to define a gas passage between the inner container and the disc. The well 110 is preferably located along the same axis as the longitudinal axis of the inner and outer containers and, as shown in FIGS. 4 and 5, has a diameter less than that of the inner container 104. The outer container is closed with a conventional scintillation vial cap or other closure, including various types of elastomer plug-type seals.

The test sample container 100 of FIGS. 4 and 5 may be used to determine the presence of and measure the biological activity of micro-organisms in a test sample by innoculating an assembled, sterile container 100 with a test sample. As in the case of the embodiments of FIGS. 1 and 2, the nutrient media may be innoculated into the container or deposited in the inner container, either in liquid or dehydrated form, during manufacture. The micro-organisms in the test sample metabolize or otherwise process the nutrient media and evolve, in the case of carbon 14-labeled nutrient-media, gaseous $^{14}CO_2$. The gas fills the headspace above the test sample/nutrient media solution, overflows into the space between the inner and outer containers, and then flows through the passage defined between the bottom surface of the inner container and the upper surface of the support disc to the absorber in the well 110 of the support disc 106. The radioactive $^{14}CO_2$ is absorbed by the absorber and causes the scintillation material to emit light flashes which can be detected by the photomultiplier tubes of a conventional laboratory type scintillation counter, schematically represented by the parallel dashed lines 22-22' in FIG. 4, and counted to provide an indication of the radiorespirometric activity of the micro-organisms in the test sample.

Experiments conducted with both embodiments, as set forth in the following examples, have demonstrated a counting efficiency substantially greater than that of the prior design in which the scintillation compound and absorber are supported on a cylindrical paper element.

EXAMPLE I

In an experiment conducted with the embodiment of FIGS. 1 and 2, 0.2 cc. of a slurry of anthracene in 2 Normal alcoholic sodium hydroxide was placed in the inner container and the solvent evaporated in a vacuum desiccator. The test sample container was assembled in accordance with the description above and the outer container innoculated with 0.2 microcuries of carbon 14-labeled sodium bicarbonate. Thereafter, one ml. of 5% phosphoric acid was added to cause the quantitative release of carbon 14-labeled carbon-dioxide and the test sample container was counted repetitively in a laboratory-type liquid scintillation counter. The detected activity reached 270,000 counts per minute, which is equivalent to an absolute counting efficiency of 61%.

EXAMPLE II

In an experiment similar to the one described above, commercially available plastic scintillator-beads were packed dry into the inner container and moistened in situ with sufficient sodium hydroxide solution to fill the interstitial spaces between the beads. The excess solution was aspirated from the top of the packed bead bed, and the solvent evaporated in a vacuum desiccator. The test sample container was innoculated with 0.2 microcuries of carbon 14-labeled sodium bicarbonate and, thereafter, 1 ml. of 5% phosphoric acid was added to cause the quantitative release of carbon 14-labeled carbon dioxide. The test sample container was then counted repetitively in a liquid scintillation counter with the detected activity reaching 185,000 counts per minute, which is equivalent to an absolute counting efficiency of 42%.

EXAMPLE III

Figure 6:
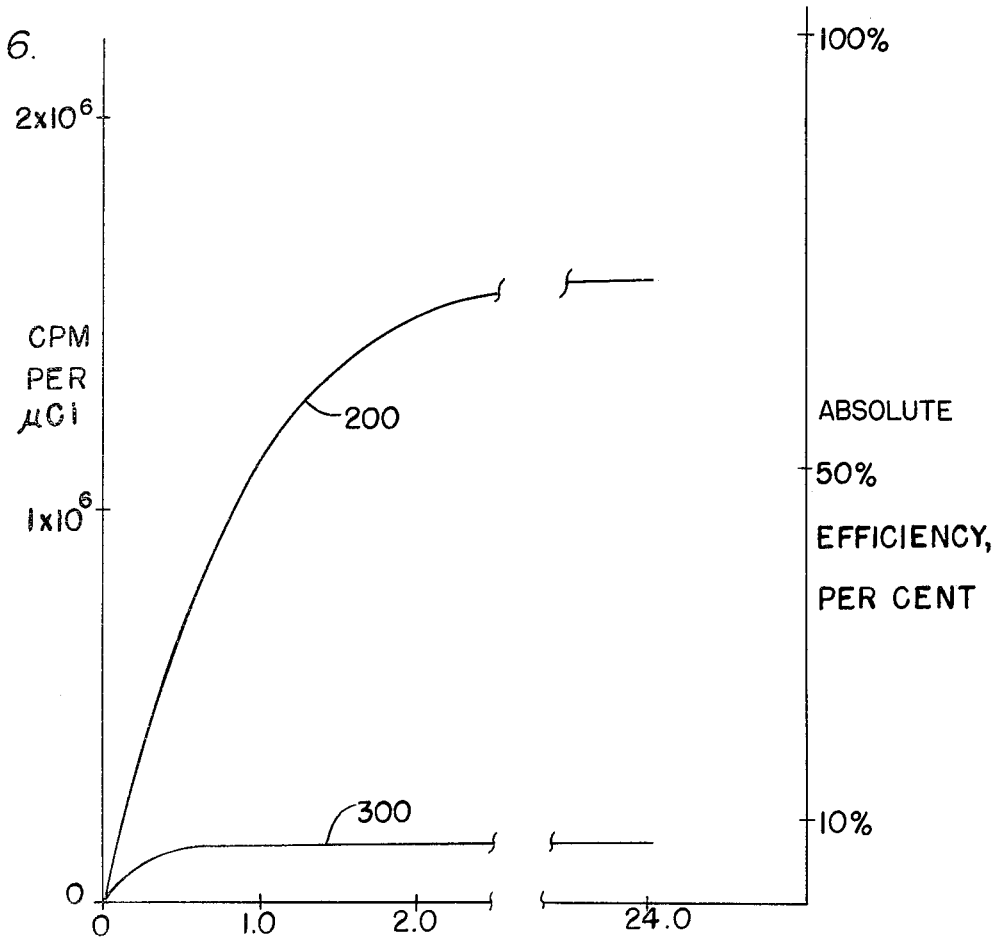
FIG. 6 is a comparative graphical representation of the count efficiency of the embodiment of FIGS. 1 and 2 and a prior art test sample container in which the left ordinate represents counts per minute per micro-Curie (cpm/$\mu$Ci), the right ordinate represents efficiency in percent (%), and the abscissa represents elapsed time in hours (hrs.).

In this experiment, a test sample container embodiment in accordance with that of FIGS. 1 and 2 and a prior art sample container as described in the aforementioned publication by the present inventor and described in U.S. Pat. No. 3,944,471 were quantitatively compared. The results of this comparison were plotted as illustrated in FIG. 6 in which the curve 200 represents the performance of the test sample container of the present invention, the curve 300 represents the performance of the prior art container, the left vertical axis represents the counts per minute per micro-curie (cpm/$\mu$Ci) detected in a liquid scintillation counter, the right vertical axis represents the absolute counting efficiency (%) where $2.22 \times 10^6$ cpm/$\mu$Ci represents 100%, and the horizontal axis represents the elapsed time in hours (hrs.). In both cases, accurately measured quantities or NaH$^{14}$CO$_3$ where deposited in each of the devices with the labeled carbon-dioxide liberated with excess phosphoric acid. As shown in the graphical comparison of FIG. 6, the test sample container in accordance with the present invention exhibits a counting efficiency of approximately 70% or about 10 times the efficiency of the prior device efficiency of 7.5%. In a related experiment using the embodiment of FIGS. 4 and 5, the test sample container exhibited an absolute efficiency of 62%, nearly as great as that of the embodiments of FIGS. 1 and 2 and approximately the same order of magnitude of improved efficiency compared to the prior art design employing the cylindrical paper absorber/fluor support.

As can be seen from the above description, the present invention provides a number of practical and performance advantages over the prior art devices, particularly the prior test sample containers which utilize a cylindrical paper scintillation compound/absorber support.

From a practical standpoint, the embodiment of FIG. 1 and the embodiment of FIG. 4, with the exception of the support disc, can be fabricated from readily-available laboratory equipment that is well suited for mass production assembly and sterilization. The embodiment of FIG. 1, in which the inner container is secured relative to the outer container by the closure member, provides a container structure which is quite rugged and which may be transported, stored, and used without special handling precautions. This feature is a marked advantage over the design which employs a relatively fragile and unsecured cylindrical paper absorber/scintillation compound support. From the cost standpoint, the test sample container uses a smaller quantity of relatively expensive scintillation compound when compared to the quantity used by the paper cylinder design.

From the performance standpoint, the inner container 14 and the support disc 16 function as lenticular elements, as was described in connection with FIG. 3, and locating the scintillation compound/fluor above or below the nutrient media/test sample mixture eliminates the problems associated with color and chemical quenching. In both of the disclosed embodiments, a clear transparent surface separates the test sample/nutrient media from the absorber/scintillation compound (the bottom of the inner container in the case of the embodiment of FIGS. 1 and 2 and the bottom of the inner container in the case of the embodiment of FIGS. 3 and 4) such that $\beta$ particle emissions from the labeled substrate are absorbed in the glass and cannot directly irradiate or impinge the scintillation compound to cause spurious light emissions.

As will be apparent to those skilled in the art, various changes and modifications may be made to the test sample container embodiments of the present invention without departing from the spirit and scope of the present invention as defined in the appended claims and the legal equivalent.

I claim:

1. An apparatus for use in radiometric analysis of the biological activity of a test sample comprising:
   (1) a first container means for containing a selected quantity of a test sample for analysis and a radionuclide-labeled nutrient media metabolizable to produce a gaseous compound that includes the radionuclide;
   (2) a second container means, enclosed within said first container, for containing a scintillation compound and an absorbent material to absorb the metabolized gas;
   (3) means for supporting said second container means in said first container means above the test sample and nutrient media; and
   (4) sealing means for sealing said first container means;

the interiors of said first container means and said second container means open to one another whereby the gaseous compound that includes the radionuclide is absorbed by the absorbent material causing the scintillation compound to emit light flashes.

2. The apparatus claimed in claim 1, wherein a bottom portion of the enclosed container shields the scintillation compound from direct $\beta$ particle irradiation from the nutrient media.

3. The apparatus claimed in claim 1, wherein:
said first container means comprises a vial adapted to fit within the test well of a scintillation counter;
said second container means comprises a micro-tube;
said sealing means comprise a split-skirt stopper to seal said vial and said stopper having a plurality of depending segments to frictionally engage said micro-tube therebetween to position said micro-tube above the test sample and nutrient media.

4. The apparatus claimed in claim 1, wherein:
said second container is located relative to said first container so that the scintillation compound and absorbent material contained therein are located in an area corresponding to an axially directed projection of the test sample/nutrient media contained within said first container.

5. An apparatus for use in radiometric analysis of the biological activity of a test sample comprising:
(1) first container means containing a selected quantity of a test sample for analysis and a radionuclide-labeled nutrient media metabolizable to produce a gaseous compound that includes the radionuclide;
(2) transparent second container means containing a scintillation compound and an absorbent material to absorb the metabolized gas;
said second container means positioned below said first container;
(3) third container means containing said first and said second container means; and
(4) sealing means for sealing said third container;
the interiors of said first and second container means open to one another whereby the gaseous compound that includes the radionuclide is absorbed by the absorbent material causing the scintillation compound to emit light flashes.

6. The apparatus claimed in claim 5 wherein:
said first container comprises a serum vial;
said second container comprises a cylindrically formed transparent element having a well formed therein to contain the scintillation compound and the absorbent material and means to space the first container thereabove; and
said third container comprises a vial adapted to fit within the test well of a scintillation counter.

7. The apparatus claimed in claim 5 wherein a bottom portion of the first container means shields the scintillation compound from direct $\beta$ particle irradiation from the nutrient media.

8. The apparatus claimed in claim 1 or 5, wherein said second container means and said first container means are coaxially positioned.

9. The apparatus claimed in claim 1 or 5 wherein the light emissions from the scintillation compound are simultaneously detectable in at least two separate directions.

10. The apparatus claimed in claim 1 or 5, wherein said second container is so shaped to function as a lenticular element for the light emissions of the scintillation compound.

11. The apparatus claimed in claim 1 or 5, wherein said nutrient media is deposited in said first container in a desiccated form.

12. The apparatus claimed in claim 1 or 5, wherein:
said second container is located relative to said first container so that the scintillation compound and absorbent material contained in said second container are located in a plane which is parallel to and spaced from the plane occupied by the test sample/nutrient media contained within said first container.

* * * * *